United States Patent

Imoto et al.

[11] Patent Number: 5,684,161
[45] Date of Patent: Nov. 4, 1997

[54] PROCESS FOR PREPARING 1-SUBSTITUTED PYRROLE-3-CARBOXYLIC ACID DERIVATIVES

[75] Inventors: Masahiro Imoto, Nishinomiya; Akira Mizuno, Kyoto; Makoto Shibata, Ashikaga; Tomoe Iwamori, Ibaraki, all of Japan

[73] Assignee: Suntory Limited, Osaka, Japan

[21] Appl. No.: 741,911

[22] Filed: Oct. 31, 1996

[51] Int. Cl.$^6$ .............................................. C07D 207/333
[52] U.S. Cl. ............................................................ 548/531
[58] Field of Search ................................................ 548/531

[56] References Cited

U.S. PATENT DOCUMENTS 4,560,700 12/1985 Sfchnettler et al.

OTHER PUBLICATIONS

J.Organ.Chem. 1982, 47, 786–791, XP000196816 A.Padwa et al.: "On the Problem of Regioselectivity in the 1,3-Dipolar Cycloaddition Reaction of Munchnones and Sydnones with Acetylenic Dipolarophiles" *p. 787, right–hand column, reaction scheme leading to compounds 15 and 16*.
Heterocycles, vol.27, No. 12, 1988, pp. 2825–2832, XP000196829 P.D. Croce et al.: "Regioselectivity in the 1,3–dipolar cycloaddition reaction of 3–methyloxazolium 5–olates with acetylenic dipolarophiles" *p. 2826, scheme 1*.

Primary Examiner—Johann Richter
Assistant Examiner—Jane C. Osweki
Attorney, Agent, or Firm—Oblon, Spivak, McClelland, Maier & Neustadt, P.C.

[57] ABSTRACT

A simple and industrially viable process for preparing a 1-substituted pyrrole-3-carboxylic acid derivative of formula (I) is provided. The process comprises reacting a compound of formula (II), a compound of formula (III), and an acid anhydride according to the following reaction,

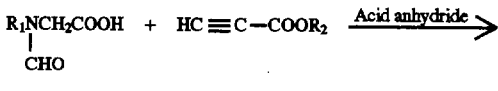

(II)  (III)

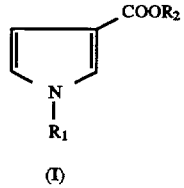

(I)

wherein $R_1$ and $R_2$ individually represent an alkyl, aralkyl, or aryl group.

3 Claims, No Drawings

PROCESS FOR PREPARING 1-SUBSTITUTED PYRROLE-3-CARBOXYLIC ACID DERIVATIVES

BACKGROUND OF THE INVENTION

1. Field of the Invention

The present invention relates to a process for preparing 1-substituted pyrrole-3-carboxylic acid derivatives useful as medicines, or as raw materials or intermediates for the synthesis of medicines.

2. Description of the Background Art

Derivatives of 1-substituted pyrrole-3-carboxylic acid are important compounds which are used as medicines for the treatment of hyperlipidemia, medicines for the improvement of periphery circulation hindrance, or as raw materials or intermediates for the synthesis of medicines. However, no industrial processes for producing derivatives of 1-substituted pyrrole-3-carboxylic acid in which the 2, 4, and 5 positions are all hydrogen atoms with sufficient economy and operational simplicity have been known.

Specifically, a method for inducing an electrophilic substitution reaction at the 3-position of a pyrrole ring, for example, is reported as a method for preparing pyrrole-3-carboxylic acid derivatives (e.g. M. Kakushima et al., J. Org. Chem., Vol.48, 3214 (1983); C. Cativiela et al., Org. Prep. Proced. Int., Vol. 18, 283 (1986); B. L. Bray et al., J. Org. Chem., Vol. 55, 6317 (1990); etc.). Due to the characteristics of pyrrole, however, the electrophilic substitution reaction on the pyrrole ring does not necessarily occur exclusively at the 3-position. There may be the case where by-products such as pyrrole-2-carboxylic acid derivatives must be separated. In addition, in these methods a specific group, such as an aryl sulfonyl group or a tri-isopropyl silyl group, is first introduced into the 1-position, and then the electrophilic substitution reaction at the 3-position is induced. For this reason, in order to obtain a compound with an alkyl group or the like substituted at the 1-position, the group which is once introduced into the 1-position must be removed before introducing the target group. This requires complicated, time-consuming reaction steps and, thus, has causes drawbacks to these methods.

As alternative methods for directly synthesizing pyrrole-3-carboxylic acid derivatives, a method for subjecting a raw material such as γ-ketoester to a cyclization reaction (for example, Japanese Patent Publication No.104658/1994), and a method for reacting p-toluenesulfonyl isocyanide and an acrylic acid ester in the presence of sodium hydride (for example, A. M. van Lausen et al., Tetrahedron Lett., Vol. 52,5337 (1972)), have been reported.

However, because the pyrrole-3-carboxylic acid derivatives produced by these methods have a hydrogen atom at the 1-position, an additional step for introducing a target group is required to obtain a compound with an alkyl group or the like substituted at 1-position. This also requires additional steps. Furthermore, the latter-mentioned methods are not economically favorable, for they require expensive reagents and produce the target compound only at a low yield.

In addition to these methods, a method for the synthesis of pyrrole-3-carboxylic acid esters having a substitutional group at the 1-position has been proposed. This method comprises reacting an ester of propiolic acid, an acid anhydride, and an α-amino acid derivative (e.g. Albert Padwa et al., J. Org. Chem., vol. 47, 786 (1982), Piero Dalla Croce et al., Heterocycles, vol. 27, 2825 (1988)). This method, however, produces only compounds with substitutional groups introduced into the 2-position and/or the 5-position.

Thus, no industrially viable processes for manufacturing 1-substituted pyrrole-3-carboxylic acid derivatives with hydrogen atoms for all of the 2, 4, and 5 positions have been known and, therefore, importance of the derivatives of 1-substituted pyrrole-3-carboxylic acid in which the 2, 4, and 5 positions are all hydrogen atoms has not been studied heretofore.

In view of this situation, the inventors of the present invention have undertaken extensive studies for the development of a process for manufacturing 1-substituted pyrrole-3-carboxylic acid derivatives and for the synthesis of medicines using derivatives of 1-substituted pyrrole-3-carboxylic acid in which the 2, 4, and 5 positions are all hydrogen atoms, as synthetic material or an intermediate. As a result, the inventors have found that 1-substituted pyrrole-3-carboxylic acid derivatives can be prepared easily, in a short period of time, and at a high yield, if an N-substituted-N-formyl glycine is used as a raw material. This finding has led to the completion of the present invention.

SUMMARY OF THE INVENTION

Accordingly, an object of the present invention is to provide a process for preparing a 1-substituted pyrrole-3-carboxylic acid derivative of the following formula (I),

(wherein $R_1$ and $R_2$ individually represent an alkyl, aralkyl, or aryl group), comprising reacting a compound of the following formula (II),

(wherein $R_1$ is as defined above), a compound of the following formula (III),

(wherein $R_2$ is as defined above), and an acid anhydride.

Other objects, features and advantages of the invention will hereinafter become more readily apparent from the following description.

DETAILED DESCRIPTION OF THE INVENTION AND PREFERRED EMBODIMENTS

Given as preferred examples of $R_1$ in formula (I) of the 1-substituted pyrrole-3-carboxylic acid derivative which is obtained by the process of the present invention are linear or branched alkyl groups such as a methyl group, ethyl group, n-propyl group, and isopropyl group, aralkyl groups such as a benzyl group and 3,4-dimethoxyphenylmethyl group, and aryl groups such as a phenyl group, 2,6-dimethylphenyl group, and naphthyl group. Preferred examples of $R_2$ include linear or branched alkyl groups such as a methyl group, ethyl group, n-propyl group, and isopropyl group, aralkyl groups such as a benzyl group, and aryl groups such as a phenyl group.

The process of the present invention comprises reacting a compound of the formula (II) with a compound of the formula (III) and an acid anhydride according to the following reaction formula.

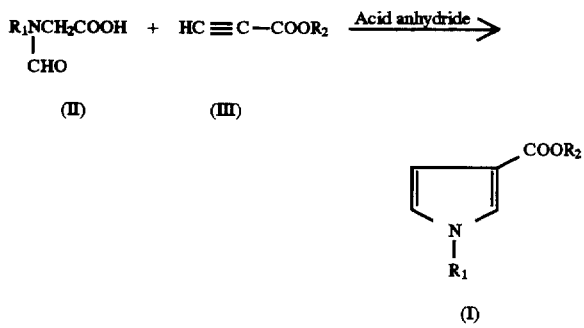

(I)

wherein $R_1$ and $R_2$ have the same meanings as defined above.

Given as examples of the acid anhydride are acetic anhydride, propionic anhydride, and the like, with acetic anhydride being particularly preferred.

The compound (II) which is the starting material can be easily manufactured by reacting a compound of the formula (IV) with acetic anhydride and formic acid according to the following reaction formula,

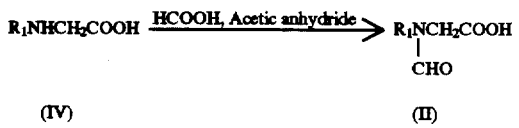

(IV)          (II)

wherein $R_1$ has the same meaning as previously defined.

N-substituted glycine such as sarcosine and N-phenyl glycine are given as specific examples of the compound (IV) which is used in this reaction.

The compound (II) can also be synthesized by a process disclosed by a publication or a process similar to the known process.

The compound (III), propiolic acid ester, is either a known compound itself or a compound which can be manufactured in accordance with a process known in the art.

The cyclization reaction of the compound (II) and the compound (III) can be carried out by adding more than one mole of an acid anhydride, such as acetic anhydride, and about 1 to 5 moles of the compound (III), for one mole of the compound (II), and heating the mixture at a temperature of 80° C. to the reflux temperatures while stirring for about 4 to 24 hours. This reaction may be carried out either in an acid anhydride (preferably in acetic anhydride) or in a solvent which is not involved in the reaction, such as toluene, in the presence of an acid anhydride. The former case is generally more preferred for achieving a high yield. Needless to say, salts of these reactants can be used instead of the compounds themselves.

To obtain the target 1-substituted pyrrole-3-carboxylic acid derivatives (I) from the reaction mixture, conventional purification means, such as distillation, recrystallization, and column chromatography, are used either individually or in combination of two or more.

The resulting 1-substituted pyrrole-3-carboxylic acid derivative (I) is useful as a medicine or as a raw material or a synthetic intermediate for medicines. When used as a raw material for the synthesis of medicines, the compound of the formula (I) is converted into the compound of (I') by removing the group $R_2$ according, for example, to the following reaction, before being submitted to various other reactions.

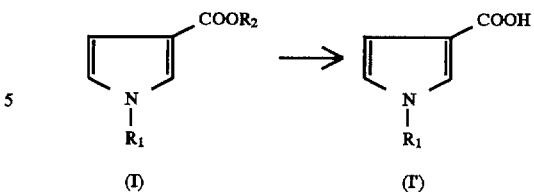

(I)          (I')

wherein $R_1$ and $R_2$ have the same meanings as previously defined.

The above reaction for converting the compound of the formula (I) into the compound of the formula (I') can be carried out by a known method, for example, by treating the compound of the formula (I) with a base such as sodium hydroxide and reacting with an acid such as hydrochloric acid.

Other features of the invention will become apparent in the course of the following description of the exemplary embodiments which are given for illustration of the invention and are not intended to be limiting thereof.

EXAMPLES

Reference Example 1

Synthesis of N-formylsarcosine 243.5 g (2.733 mole) of sarcosine and 1500 g (32.58 mole) of formic acid were transferred into a reaction vessel, and 887.4 g (8.691 mole) of acetic anhydride was added dropwise to the mixture over 30 minutes while cooling and stirring. The resulting mixture was stirred for three hours at room temperature.

The resulting light-yellow reaction mixture was concentrated under vacuum, 50 ml of water was added to the residue, and the resulting mixture was evaporated under vacuum. This operation was repeated, then, 50 ml of toluene was added to the residue and the mixture was evaporated under vacuum. After repeating this operation, seed crystals of N-formyl-sarcosine were added to crystallize the residue. After completely removing the solvent by a pump, 1200 ml of ethyl acetate was added and the mixture was stirred over a hot water bath at 70° C. until the crystals were completely dissolved. Seed crystals were again added and the mixture was stirred overnight. After stirring for one hour at 0° C., the precipitated crystals were collected by filtration to obtain 278.6 g of the title compound (yield 87.1%).

Properties: colorless powdery crystals

Melting point: 85.0–87.0° C.

Reference Example 2

Synthesis of N-benzyl-N-formylglycine 19.33 g (100 mmole) of N-benzylglycine ethyl ester and 109.6 g (2.38 mol) of formic acid were transferred into a reaction vessel. Then, 32.46 g (316 mmole) of acetic anhydride was added dropwise over about 15 minutes while cooling and stirring. The mixture was continuously stirred for one hour at 0° C. and two hours at room temperature.

The reaction mixture was concentrated under vacuum and 500 ml of ethyl acetate was added to the residue. The organic layer was washed with a half saturated aqueous solution of potassium carbonate, water, a 15% aqueous solution of citric acid, water, and a saturated brine, in that order, dried over anhydrous sodium sulfate, and concentrated under vacuum to obtain 21.70 g of a light-yellow oily substance.

98 ml of 2N sodium hydroxide aqueous solution was added to the resulting oily substance and the mixture was stirred for 30 minutes at 50° C. and two hours at room temperature.

The reaction mixture was washed with ethyl ether and 6 N hydrochloric acid aqueous solution was added to the water layer while stirring to make the solution acidic. After the addition of sodium chloride, the mixture was extracted with ethyl acetate (3 times). The extract was washed with saturated brine, dried over anhydrous sodium sulfate, and concentrated under vacuum. The resulting crude crystals were recrystallized from chloroform-isopropyl ether to obtain 17.27 g of the title compound (yield 89.4%).

Properties: colorless prismatic crystals
Melting point: 124.0–127.0° C.

Reference Example 3

Synthesis of N-formyl-N-phenylglycine 7.56 g (50 mmole) of N-phenyl glycine and 54.87 g (1.19 mmole) of formic acid were transferred into a reaction vessel and 16.23 g (159 mol) of acetic anhydride was added dropwise over about 10 minutes while cooling and stirring. The reaction mixture was stirred for one hour at 0° C. and for two hours at room temperature. The resulting reaction mixture was concentrated under vacuum to obtain crude crystals. The crystals were recrystallized from ethanol-isopropyl ether to obtain 7.47 g of the title compound (yield 83.4%).

Properties: light-yellow powdery crystals
Melting point: 169° C. (decomposed)

Example 1

Synthesis of ethyl 1-methyl-3-pyrrolecarboxylate (1)

A mixture of 117.1 g (1 mole) of N-formylsarcosine prepared in the Reference Example 1, 98.10 g (1 mole) of ethyl propiolate, and 638 ml of acetic anhydride was stirred using a magnetic stirrer over an oil bath at 130° C. for 22 hours. The reaction mixture was concentrated under vacuum. 100 ml of toluene was added to the residue and the mixture was evaporated under reduced pressure. This procedure was repeated to obtain a brown oily substance. This oily substance was distilled under vacuum to obtain 109.19 g (yield 71.3%) of a colorless or light-yellow oil of the title compound as fractions with a boiling point of 103°–104° C. at 4 mmHg.

IR(film cm$^{-1}$): 1701, 1544, 1250, 1218, 1113, 1026, 965, 763 NMR (measured in CDCl$_3$ using TMS as an internal standard/400 MHz/$\delta_{ppm}$)

1.32(3H, t, J=7.1 Hz), 3.66(3H, s) 4.26(2H, q, J=7.1 Hz), 6.54(1H, m), 6.57 (1H, m), 7.23(1H, t, J=1.9 Hz)

Example 2

Synthesis of ethyl 1-methyl-3-pyrrolecarboxylate (2)

The same procedure as in Example 1 was carried out using 15.64 g (0.134 mole) of N-formylsarcosine, 49.00 g (0.499 mole) of ethyl propiolate, and 107 ml of acetic anhydride to obtain 18.08 g (yield 88.4%) of the title compound.

Example 3

Synthesis of methyl 1-methyl-3-pyrrolecarboxylate

A mixture of 9.52 g (0.0813 mole) of N-formylsarcosine prepared in the Reference Example 1, 25.56 g (0.304 mole) of methyl propiolate, and 65 ml of acetic anhydride was stirred using a magnetic stirrer over an oil bath at 130° C. for 24 hours. The reaction mixture was concentrated under vacuum. 30 ml of toluene was added to the residue and the mixture was evaporated under reduced pressure. This procedure was repeated to obtain a brown oily substance. This oily substance was distilled under vacuum to obtain 9.01 g (yield 79.6%) of a colorless or light-yellow oil of the title compound as fractions with a boiling point of 93°–96° C. at 4 mmHg.

IR(film cm$^{-1}$): 1705, 1543, 1442, 1250, 1222, 1117, 764

NMR (measured in CDCl$_3$ using TMS as an internal standard/400 MHz/$\delta_{ppm}$)

3.65(3H, s), 3.78(3H, s), 6.51–6.58(2H, m), 7.22(1H, m)

Example 4

Synthesis of ethyl 1-benzyl-3-pyrrolecarboxylate

A mixture of 1.93 g (10 mmole) of N-benzyl-N-formyl-glycine obtained in the Reference Example 2, 3.65 g (37.2 mmole) of ethyl propiolate, and 10 ml of acetic anhydride was stirred using a magnetic stirrer over an oil bath at 130° C. for 20 hours. The reaction mixture was concentrated under vacuum. 15 ml of toluene was added to the residue and the mixture was evaporated under reduced pressure. This procedure was repeated to obtain a brown oily substance. This oily substance was purified using silica gel column chromatography (No. 9385 silica gel, manufactured by Merck Co., eluted with ethyl acetate:hexane=1:3 v/v) to obtain 2.156 g (yield 94.0%) of a light-yellow oil of the title compound.

IR(film cm$^{-1}$): 2980, 1702, 1541, 1508, 1455, 1373, 1221, 1112, 1027, 968, 763, 711

NMR (measured in CDCl$_3$ using TMS as an internal standard/400 MHz/$\delta_{ppm}$)

1.33(3H, t, J=7.1 Hz), 4.26(2H, q, J=7.1 Hz), 5.06(2H, s), 6.59–6.64(2H, m), 7.27–7.39(4H, m)

Example 5

Synthesis of ethyl 1-phenyl-3-pyrrolecarboxylate

A mixture of 2.69 g (15 mmole) of N-formyl-N-phenyl-glycine prepared in Reference Example 3, 5.47 g (55.8 mmole) of ethyl propiolate, and 15 ml of acetic anhydride was stirred using a magnetic stirrer over an oil bath at 130° C. for 22 hours. The reaction mixture was concentrated under vacuum. 22 ml of toluene was added to the residue and the mixture was evaporated under reduced pressure. This procedure was repeated to obtain a brown oily substance. This oily substance was purified using silica gel column chromatography (No. 9385 silica gel, manufactured by Merck Co., eluted with ethyl acetate:hexane=1:5 v/v) to obtain 2.8949 (yield 89.6%) of a light-yellow oil of the title compound.

IR(film cm$^{-1}$): 1709, 1600, 1544, 1509, 1260, 1224, 1138, 757, NMR (measured in CDCl$_3$ using TMS as an internal standard/ 400 MHz/$\delta_{ppm}$) 1.36(3H, t, J=7.1Hz), 4.31(2H, q, J=7.1Hz), 6.76 (1H, br.s), 7.01(1H, br.s), 7.31(1H, t, 5:7.2Hz), 7.34–7.50(4H, m), 7.68(1H, s)

Reference Example 4

7.66 g (50 mmole) of ethyl 1-methyl-3-pyrrolecarboxylate prepared in Example 1 and 37.5 ml (75 mmole) of 2N sodium hydroxide aqueous solution were charged into a reaction vessel and refluxed for two hours. The reaction mixture was cooled to 0° C. and about 7 ml of 6N hydrochloric acid solution was added while stirring. After the addition of 15 g of sodium chloride, the mixture was stirred for one hour over an ice-acetone bath to collect precipitated crystals. The crystals were washed with cold water and dried under reduced pressure to obtain 5.77 g (yield 92.2%) of colorless or light-yellow powdery crystals of 1-methyl-3-pyrrolecarboxylic acid.

Because the reaction used in the process of the present invention is not a substitution reaction on a pyrrole ring, the process does not involve side production of pyrrole-2-carboxylic acid derivatives. Thus, there is no need for the process to have a complicated step for the separation of the by-products. An additional advantage in the process of the present invention is in its capability of directly producing a pyrrole-3-carboxylic acid derivative with a substituted alkyl group or the like introduced into the 1-position.

Moreover, non-use of any dangerous reagents and a smaller number of reaction steps ensure more simple operations and a drastically shorter period of time for the processing. In addition, use of a readily available and inexpensive raw material and a high production yield make the process for the manufacture of 1-substituted pyrrole-3-carboxylic acid derivatives industrially viable.

Furthermore, the 1-substituted pyrrole-3-carboxylic acid derivatives of the present invention will make it easy to develop medicines using these derivatives as raw materials.

Obviously, numerous modifications and variations of the present invention are possible in light of the above teachings. It is therefore to be understood that, within the scope of the appended claims, the invention may be practiced otherwise than as specifically described herein.

What is claimed is:

1. A process for preparing a 1-substituted pyrrole-3-carboxylic acid derivative of the following formula (I),

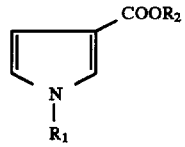
(I)

wherein $R_1$ and $R_2$ individually represent an alkyl, aralkyl, or aryl group, comprising reacting a compound of the following formula (II),

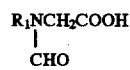
(II)

wherein $R_1$ is as defined above, a compound of the following formula (III),

(III)

wherein $R_2$ is as defined above, and an acid anhydride.

2. The process according to claim 1, wherein the acid anhydride is acetic anhydride.

3. The process according to claim 1, wherein the reaction is carried out in acetic anhydride.

* * * * *

UNITED STATES PATENT AND TRADEMARK OFFICE
CERTIFICATE OF CORRECTION

PATENT NO. : 5,684,161
DATED      : November 4, 1997
INVENTOR(S): Masahiro IMOTO, et al.

It is certified that error appears in the above-identified patent and that said Letters Patent is hereby corrected as shown below:

On the title page, item [30] has been omitted. It should be:

--[30]    Foreign Application Priority Data
    Nov. 2, 1995   [JP]   Japan  .........   7-308540--

Signed and Sealed this

Thirtieth Day of December, 1997

Attest:

BRUCE LEHMAN

Attesting Officer

Commissioner of Patents and Trademarks